(12) United States Patent
Vitrac et al.

(10) Patent No.: US 10,980,736 B2
(45) Date of Patent: Apr. 20, 2021

(54) COCONUT SHELL EXTRACTS, COMPOSITIONS CONTAINING SAME AND USES

(71) Applicant: Laboratoire Phenobio, Saucats (FR)

(72) Inventors: Caroline Vitrac, Saint Medard d'Eyrans (FR); Xavier Vitrac, Saint Medard d'Eyrans (FR)

(73) Assignee: Laboratoire Phenobio, Saucats (FR)

( * ) Notice: Subject to any disclaimer, the term of this patent is extended or adjusted under 35 U.S.C. 154(b) by 0 days.

(21) Appl. No.: 16/084,826

(22) PCT Filed: Mar. 15, 2017

(86) PCT No.: PCT/EP2017/056110
§ 371 (c)(1),
(2) Date: Sep. 13, 2018

(87) PCT Pub. No.: WO2017/158014
PCT Pub. Date: Sep. 21, 2017

(65) Prior Publication Data
US 2019/0076350 A1    Mar. 14, 2019

(30) Foreign Application Priority Data
Mar. 15, 2016   (FR) ...................................... 1652155

(51) Int. Cl.
| | | |
|---|---|---|
| *A61K 8/34* | (2006.01) | |
| *A61Q 19/02* | (2006.01) | |
| *A61Q 19/08* | (2006.01) | |
| *A61K 8/9794* | (2017.01) | |
| *A61K 8/368* | (2006.01) | |
| *A61K 8/97* | (2017.01) | |
| *A61K 8/49* | (2006.01) | |

(52) U.S. Cl.
CPC ............ *A61K 8/9794* (2017.08); *A61K 8/347* (2013.01); *A61K 8/368* (2013.01); *A61K 8/498* (2013.01); *A61K 8/4973* (2013.01); *A61K 8/97* (2013.01); *A61Q 19/02* (2013.01); *A61Q 19/08* (2013.01); *A61K 2800/522* (2013.01); *A61K 2800/5922* (2013.01); *A61K 2800/782* (2013.01); *A61K 2800/805* (2013.01)

(58) Field of Classification Search
None
See application file for complete search history.

(56) References Cited

U.S. PATENT DOCUMENTS

2008/0118449 A1    5/2008  Alvin

FOREIGN PATENT DOCUMENTS

JP         2013151458 A       8/2013

OTHER PUBLICATIONS

Akiyele et al. (In vitro antibacterial properties of crude aqueous and n-hexane extracts of the husks of cocos nucifera, Molecules 2011, vol. 16 2135-2145) (Year: 2011).*

(Continued)

*Primary Examiner* — Melissa S Mercier
(74) *Attorney, Agent, or Firm* — Ann Skerry; Thoburn Dunlap (57) ABSTRACT

A coconut shell extract characterized by a particular level of trans-piceatanol and cosmetic and/or dermatological compositions comprising the coconut shell extract. Methods comprising a cosmetic application of at least one of compositions.

14 Claims, 7 Drawing Sheets

(56) References Cited

OTHER PUBLICATIONS

Venkataraman et al. (Antifungal activity of the alcoholic extract of coconut shell-Cocos nucifera Linn, Journal of Ethnopharmacology, 2 (1980) 291-293. (Year: 1980).*
Liang et al. (Application of Sub-Critical Water Extraction in Pharmaceutical Industry, Journal of Materials Science and Chemical Engineering, 2013, 1,1-6) (Year: 2013).*
Venkataraman S. et al., "Antifungal activity of the alcoholic extract of coconut shell—Cocos nucifera Linn", Journal of Ethnopharmacology, Jan. 1980, pp. 291-293, vol. 2, No. 3.
Akinyele, T. et al., "In-Vitro Antibacterial Properties of Crude Aqueous and n-Hexane Extracts of the Husk of Cocos nucifera", Molecules, Mar. 2011, pp. 2135-2145, vol. 16, No. 12.
Akinpelu K. et al., "Probably mechanisms of biocidal action of Cocos nucifera Husk extract and fractions on bacteria solates", BMC Complementary and Alternative Medicine, Apr. 2015, pp. 1-9, vol. 15, No. 1.
Rodrigues S. et al., "Optimization of ultrasound extraction of phenolic compounds from coconut (Cocos nucifera) shell powder by response surface methodology", Ultrasonics Sonochemistry, Oct. 2007, pp. 95-100, vol. 15, No. 1.
Dey G. et al., "Detection of major phenolic acids from dried mesocarpic husk of mature coconut by thin layer chromatography", Industrial Crops and Products, Sep. 2003, pp. 171-176, vol. 18, No. 2.
Liang X et al., "Application of Sub-Critical Water Extraction in Pharmaceutical Industry", Journal of Materials Science and Chemical Engineering, Jan. 2013, pp. 1-6, vol. 1, No. 5.
Yokozawaa T. et al., "Piceatannol Inhibits Melanogenesis by Its Antioxidative Actions", Biological & Pharmaceutical Society of Japan, Nov. 2007, pp. 2007-2011, vol. 30, No. 11.
XP002760929, Database WPI, Week 201355, Aug. 8, 2013, Thomas Scientific, London, GB; AN 2013-M13330.

* cited by examiner

COCONUT SHELL EXTRACTS, COMPOSITIONS CONTAINING SAME AND USES

CROSS-REFERENCE TO RELATED APPLICATIONS

This application is US national stage application of PCT/EP2017/056110 filed Mar. 15, 2017 which claims a benefit of priority to French patent application 1652155 filed Mar. 15, 2016, the entire disclosure of both applications is herein incorporated by reference.

TECHNICAL FIELD

The present invention concerns the use of a coconut shell extract in compositions for topical applications. The object of the invention is in particular a coconut shell extract, as well as compositions including it and a cosmetic process for improving the state of the skin.

BACKGROUND

The skin, the largest organ of the human body, forms a protective barrier for the body against the external environment and also provides other vital functions. Cosmetic research consists in proposing solutions capable of preserving these natural functions and to protect the skin from aggressions endured daily.

For the last several years, products of natural origin have been proposed, in particular products from vegetable based raw materials. Nevertheless, these products are not always satisfactory and there is still a need for new natural products capable of protecting and effectively improving the condition of the skin, in particular products capable of fighting the signs of aging skin and depigmenting and brightening products.

SUMMARY

The present invention's objective is to respond to this need by providing a natural extract of coconut shell.

The coconut palm (*Cocos nucifera* L.) is a species of palms of the Arecaceae family, present throughout the humid intertropical zone. It is the only species of the *Cocos* genus. The coconut tree has a foliar crown composed of about thirty green palms. Each palm is 4 to 7 meters long and has about 200 leaflets along the rachis. The inflorescences are composed of spikelets with female flowers at their base and male flowers at their tips. The fruit, located in the axil of each palm, are called drupes, or more commonly "coconut".

The coconut is made up of several successive envelopes. The outermost, called mesocarp, fluff, or coir, is first green then brownish when ripe. It is tough and fibrous. It is used for example in the making of fabrics, brushes, mats, rugs, mattresses, insulation panels and packaging. Once removed, the nut has a hard brown shell: the seed. Oblong or spherical shaped, it is reinforced with three more or less noticeable longitudinal ribs. A thin, reddish-brown film, the seminal integument, forms a link between the shell and a white or almond colored albumen, shiny, 10 to 15 mm thick. This kind of pulp is used to make coconut milk, obtained after grinding the pulp with water and filtering. This extracted pulp is dried in the sun until the nearly total disappearance of its water content, which must not exceed 6%, to obtain copra. Copra is used, in one part, in making coconut oil, secondly for human consumption in the manufacturing of margarine, and partly in soap and cosmetic manufacturing, particularly in monoï combined with the tiara flower of Tahiti. More than 90% of coprah oil consists of saturated fats with trace amounts of some unsaturated fatty acids. Finally, an opalescent and sweet liquid occupies up to three quarters of the internal cavity of the nut. It is commonly called "coconut water". This liquid is the nut's own fresh water reserve, intended to allow it to germinate, whatever the external conditions.

The coconut shell (endocarp), with a high PCI (low heating value), a high density and excellent homogeneity is particularly interesting and therefore frequently used as a fuel, for waste burning furnaces for example.

In addition to these uses, shell powder is used in the industry as a plastic filler or for the making of glues. Carbonization allows the production of coal that can be used as fuel for private individuals or serve as raw material for the activation and manufacturing of activated carbon. The exceptional properties of activated carbon from coconut hulls allow it to be used as a filter for water, smoke, gas, notably in the industries of water distribution, food, nuclear, etc.

Surprisingly, according to the invention, coconut shell extracts present positive effects on the skin in protecting it and improving its natural functions.

The invention therefore targets cosmetic and/or dermocosmetic compositions intended for topical application, using a coconut shell extract as active ingredient. Applied to the skin, these compositions allow improvement to its condition. In particular, they make it possible to prevent and/or reduce and/or treat signs of aging skin and/or mucous membranes and/or the hair, and also to lighten the complexion and/or reduce brown spots on the skin.

The purpose of the invention is also a particular coconut shell extract comprising between 50 and 200 ppm trans-piceatannol in fluid weight of liquid extract when the extract is in liquid form, and between 0.2 and 0.8% of trans-piceatannol in dry weight when the extract is in solid form.

The invention also relates to a specific process particularly suitable for obtaining such an extract. The presence of these specific phenolic compounds, which are found only in the endocarp of the fruit (shell), plays an important role in the effect on the skin, from the coconut shell extracts.

The invention is now described in detail with reference to the annex figures.

DETAILED DESCRIPTION

In the present application, the singular form of a word includes the plural, and vice versa, unless the context clearly indicates otherwise. Thus, the references "a", "an", and "the" include the plural of these terms. For example, the reference to "an extract" or "a composition" includes a plurality of such "extracts" or "compositions".

For the purposes of the invention, the term "active ingredient" is intended to mean a substance having an effect on the skin allowing improvement in appearance and/or functions and/or to protect it. It may be a cosmetic active ingredient or a dermatological active ingredient.

For the purposes of the invention, by coconut shell extract we mean an ensemble of molecules obtained from coconut shell.

By coconut shell we mean the endocarp of the coconut fruit.

By ppm we mean parts per million or mg/kg.

According to a first aspect, the subject of the invention is therefore cosmetic and/or dermatological compositions for topical application, including, as active ingredient, a coconut shell extract.

According to the invention, the composition preferably includes from 0.01 to 10% in weight of coconut shell extract relative to the total weight of the composition.

In addition to the coconut shell extract, the composition according to the invention also includes one or more cosmetically or dermatologically acceptable excipients. They may be, for example, dyes, film-forming active agents, surfactants, fragrances, preservatives, emulsifiers, gelling agents, vegetable oils, glycols, vitamins, antioxidants, UV filters, etc.

The composition may equally contain one or more other cosmetic and/or dermatological active ingredients, natural and/or synthetic and of animal and/or vegetable origin.

The composition may be obtained by the simple mixing of the constituents, or by any suitable method known to those skilled in the art.

The composition may be in any form suitable for topical application to the skin and/or the mucous membranes and/or the hair, in particular in the form of cream, emulsion, milk, ointment, lotion, oil, aqueous solution, hydro-alcoholic solution, glycolic solution, powder, patch or spray.

Preferably, the coconut shell extract present in the compositions according to the invention is an extract containing polyphenols, in particular an extract comprising between 5 and 40% of polyphenols by weight of dry matter of the extract, dosed according to the Folin-Ciocalteu method.

The coconut shell extract present in the compositions according to the invention may be obtained by any extraction method known to those skilled in the art, adapted for coconut shells. It can be in solid or liquid form. Preferably, it is a liquid extract. In this case, it is preferably stabilized with glycerin before being incorporated into the composition.

According to a particularly suitable method, the coconut shell extract is a particle extract, as described in the following.

In fact, the invention targets a particle coconut shell extract, liquid or solid, including trans-piceatannol in an effective amount, in particular a coconut shell extract including at least between 50 and 200 ppm of trans-piceatannol by weight of liquid extract when the extract is in liquid form, or between 0.2% and 0.8% of trans-piceatannol by weight of dry extract when the extract is in solid form (particularly in powder form). The trans-piceatanol dosage is carried out by high performance liquid chromatography (HPLC) whether the extract is in liquid or solid form.

Piceatannol is a compound whose chemical structure is similar to that of resveratrol, a compound whose health benefits have been known for several years. The chemical structure of trans-piceatanol is as follows:

The coconut shell extract includes at least one other molecule in addition to trans-piceatanol. Preferentially, this other molecule (or these other molecules) is (are) chosen from:

scirpusin A, from the formula:

and/or scipusin B, from the formula:

and/or hydroxybenzoic acid, in particular 4-hydroxybenzoic acid from the formula:

Even more preferably, the coconut shell extract includes:
- between 2 and 20 ppm of scirpusin A and between 5 and 50 ppm of scipusin B by liquid extract weight if the extract is liquid, or between 0.008 and 0.08% of scirpusin A and between 0.02 and 0.2% of scipusin B, dry extract weight if the extract is solid, and/or
- between 10 and 1000 ppm of hydroxybenzoic acid by liquid extract weight, or between 0.04% and 4% of hydroxybenzoic acid by weight of solids if the extract is solid The coconut shell extract according to the invention, contains preferably between 5 and 40% polyphenols by dry matter weight of the extract no matter what its form.

The coconut shell extract according to the invention, in order to contain between 50 and 200 ppm of trans-picéatannol by liquid extract weight, is preferably obtained by solid-liquid extraction in a solvent selected from the group consisting of subcritical water, hydro-alcoholic, hydro-glycerolic and/or hydro-glycol solvents and mixtures thereof. Similarly, the coconut shell is preferably dried and/or milled before extraction.

A solid-liquid extraction process with an acceptable hydro-alcoholic solvent to obtain an extract according to the invention includes the following steps:
- Preferably grinding the plant material, for example using a crusher, to obtain particles with a particle size of 0.5 to 10 mm,
- solid/liquid extraction: the crushed coconut shell is mixed with an aqueous-alcoholic solution in a ratio of between 150 and 200 g of shell per liter of solvent, preferably an ethanol solution of 96% or of methanol/water 50/50 (v/v), at a temperature between 20° C. and 30° C. for a period of between 4 and 24 hours
- separation of solid and liquid parts, clarification by filtration or centrifugation,
- removal of the organic solvent by vacuum concentration, for example with Rotavapor,
- drying the aqueous concentrate by lyophilization or atomization or in a vacuum oven.

A solid-liquid extraction method with an acceptable hydro-glycolic solvent to obtain an extract according to the invention includes the following steps:
- preferably crushing the plant material, for example using a grinder, to obtain particles having a particle size of 0.5 to 10 mm,
- solid/liquid extraction: the crushed coconut is mixed with a hydro-glycolic solution in a ratio of between 150 and 200 g of shell per liter of solvent, preferably a glycerin/water solution 50/50 (v/v) at a temperature of between 20° C. and 40° C. for a period of time between 12 and 24 hours,
- separation of solid and liquid parts, clarification by filtration or centrifugation.

A solid-liquid extraction method with an acceptable hydro-glycolic solvent to obtain an extract according to the invention includes the following steps:
- Preferably grinding the plant material, for example using a crusher, to obtain particles with a particle size of 0.5 to 10 mm,
- solid/liquid extraction: the crushed coconut shell is mixed with a hydro-glycolic solution in a ratio of between 150 and 200 g of shell per liter of solvent, preferably a solution of propylene glycol/water 60/40 (v/v) or 70/30 (v/v), at a temperature between 20° C. and 30° C. for a period of between 4 and 24 hours,
- separation of solid parts and liquid, clarification by filtration or centrifugation.

According to a preferred variant, the coconut shell extract according to the invention is obtained by extraction with subcritical water. Under certain conditions of temperature and pressure, the physico-chemical properties of the water are modified and the water goes into the subcritical state. At temperatures above 100° C. but below the critical point (374° C.) and at pressures below 221 bar, the water remains in the liquid state but becomes a solvent with particularly interesting properties in the field of plant extraction. Under these conditions, the viscosity and the surface tension of subcritical water are lower than that of water at room temperature, its diffusivity increases and its dielectric constant becomes close to that of organic solvents such as ethanol or acetone. This results in better penetration of the solvent into the vegetable matrix, improved mass transfer and a faster diffusion rate, thus higher extraction yielded within very short contact times.

In the case of extraction by subcritical water, the coconut shell is also preferably dried and/or crushed before being extracted.

Preferably, the coconut shell extract according to the invention is obtained by a process which consists of a water extraction in the subcritical state in dynamic mode or in batch, carried out at a temperature between 100° C. and 220° C. and at a pressure above 20 bar, sufficient to maintain the water in the liquid state. In particular, the extraction in dynamic mode is carried out by the use of the following steps:
- Preferably grinding the plant material, for example using a crusher, to obtain particles with a particle size of 0.5 to 10 mm,
- between 15 and 20 g of crushed coconut shell is introduced into a 30 ml volume reactor, which is placed in an oven previously heated to a temperature above 100° C., and then the water is pumped through the reactor, under the following operating conditions:
- flow rate: between 1 and 10 ml/min, preferably between 2 and 6 ml/min,
- water temperature: between 100 and 220° C., preferably between 120 and 200° C.,
- pressure: between 20 and 50 bars, preferably 30 bars.
- after passing 100 to 150 ml of water in the subcritical state through the plant material, the aqueous extract is recovered.

One of the advantages of this method is that no separation of the solid parts and the liquid is necessary.

In the case of a liquid formulation, the aqueous extract is mixed with glycerin in proportions of between 50 and 80% by glycerin weight, in order to be microbiologically stabilized.

In the case of a formulation in powder form, the aqueous extract is directly dried by lyophilization or atomization or in a vacuum oven.

The coconut shell extracts and in particular the coconut shell extracts according to the invention have properties enabling it to improve the state of the skin and to maintain or restore its natural functions and to protect it against external aggression, all of these applying to healthy people who are not sick.

The coconut shell extracts and in particular the coconut shell extracts according to the invention notably exhibit:
an antioxidant effect,
an anti-glycation effect, and
an inhibitory effect of tyrosinase.

The compositions and extracts according to the invention can therefore be used in cosmetic processes, and the invention is specifically aimed at a cosmetic process for the care of the skin which consists in applying to the skin (in topical application) a cosmetic composition containing a coconut shell extract.

In particular, the invention can be used to initiate a cosmetic process for preventing and/or reducing and/or treating signs of aging of the skin and/or mucous membranes and/or hair.

Different mechanisms come into play during skin aging: oxidative processes, protein glycation, uncontrolled proteolysis of macromolecules in the extracellular matrix, errors made during DNA repair mechanisms, etc.

One of the mechanisms involved in aging is the radical theory that highly reactive molecules, linked to oxygen, are responsible for harmful cellular effects. These highly reactive molecules are called free radicals or Reactive Oxygen Species (ROS). Free radicals are unstable molecules produced by mitochondria during enzymatic reactions. They are generated by the normal functioning of the body. Certain other factors lead to an increase in the production of free radicals (tobacco, pollution, sun, pesticides, stress, unbalanced diet rich in sugars and fats . . . ). These chemical species have a high reactivity and can cause significant molecular disorders: lipid peroxidation of biological membranes, protein alterations involving both structural proteins and more functional proteins such as enzymes or hormones. Thus, the action of free radicals contributes in accelerating the aging process.

Proteins can be altered by free radicals but also by glycation. Glycation is a non-enzymatic reaction between a reducing sugar (glucose or fructose) and the free amino group of an amino acid, usually lysine or arginine. Through several steps, glycation generates, in its early phases, the formation of an unstable aldimine bond (Schiff's base), capable of undergoing a molecular rearrangement called Amadori rearrangement, leading to the formation of a stable ketoamine linkage. The products formed are called Amadori products (in the case of aldoses), or Heyns (in the rarest case of ketoses). Subsequently, they undergo many oxidative reactions, forming reactive intermediates (including aldehydes such as methylglyoxal) and resulting in the formation of complex structural compounds, often fluorescent, called advanced glycation products (AGE, Advanced-Glycation End product). Glycation modifies the structure of proteins (formation of cross-links, modifications of antigenicity), but also their functions (enzymatic or biological activity), and their relationship with cells, primarily with inflammatory cells.

Glycation products are mostly detected on molecules with a slow turnover rate, such as collagen I and III or elastin. During the aging process, the intra- and intermolecular bonds will accumulate, which will cause changes in the biomechanical properties of the skin with an alteration of the elasticity associated with stiffening which leads to the appearance of wrinkles.

The links between glycation and oxidative stress are very close, and the two phenomena are often grouped under the term "glycoxidation". All stages of glycoxidation generate the production of oxygen free radicals, and some steps are shared with those of lipid peroxidation.

Thus, by trapping free radicals and inhibiting the glycation of proteins at the same time, the extracts and compositions according to the invention can delay the aging of the skin.

Furthermore, the extract and/or the composition according to the invention can be used to implement a cosmetic method for lightening the complexion of the skin and/or to prevent and/or reduce dark spots on the skin. The natural pigmentation of the skin is due to the production of melanin by the melanocytes of the epidermis. Melanin synthesis (melanogenesis) is increased under the action of UV rays which induces tanning whose physiological function is to protect the skin against UVs. Various dysfunctions of the melanin production mechanism (by excess external aggressions, by hormonal disturbances or aging) cause the appearance of brown spots, particularly in the form of freckles, sun spots or age spots (respectively solar lentigo and senile lentigo). To act on skin pigmentation, you can use products that alter the melanin or products that inhibit its synthesis by melanocytes or its distribution in epidermal cell layers. In the melanin biosynthetic chain, various enzymes and intermediates can serve as targets for inhibitors. This is particularly the case of tyrosinase which catalyzes the formation of dopaquinone and then of dopachrome from L-DOPA. Thus, by acting on the activity of tyrosinase in skin cells, the extracts and compositions according to the invention have a depigmenting effect on the skin.

The invention is now illustrated through examples and test results demonstrating the effect of the active ingredient and compositions including it.

EXAMPLES

Example 1: Coconut Shell Extract Obtained by Solid-Liquid Extraction with a Hydro-Alcoholic Solvent This first example of an extract according to the invention is obtained by a process consisting of the following steps:
Crushing the plant material using a crusher to obtain particles with a particle size of 1 to 2 mm;
Solid/liquid extraction: mixing 16.5 g of coconut shell milled in 100 ml of a hydroalcoholic solution methanol/water 50/50 (v/v) at room temperature for 24 hours;
Separation of solids and liquids by centrifugation at 9000 rpm for 10 minutes;
Eliminating organic solvent by vacuum concentration in a Rotavapor;
Drying the aqueous concentrate in a vacuum oven.

The polyphenol extract in powder form is dissolved in ultrapure water per 10 mg/ml, and then the solution is filtered through a 0.45 µm PTFE filter. 10 µl of solution are then injected onto a Prontosil column (C18, reverse phase, 250×4.6 mm, 5 µm). The solvents used are: A: H2O/TFA 1% (1 L/5 mL) and B: ACN/TFA 1% (1 L/5 mL). The separation gradient is as follows, at a flow rate of 0.8 mL/minute:

TABLE 1

| Gradient separation used in HPLC | |
| --- | --- |
| Time (min.) | % B |
| 0 | 0 |
| 35 | 55 |
| 36 | 100 |

TABLE 1-continued

Gradient separation used in HPLC

| Time (min.) | % B |
|---|---|
| 37 | 100 |
| 38 | 0 |
| 40 | 0 |

Figure 1:
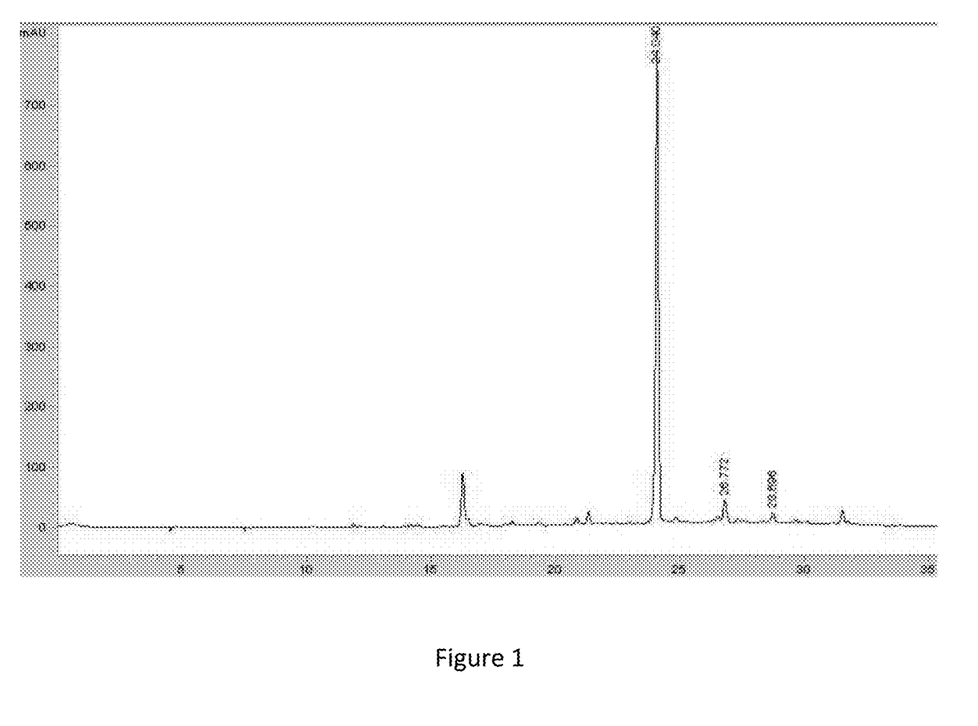
FIG. 1 shows the chromatogram at 306 nm of the extract of Example 1 according to the invention.

The chromatogram at 306 nm of the extract obtained is shown in FIG. 1.

The extract obtained has a total polyphenol content of 0.542 mg/mL of liquid extract and a trans-piceatannol content of 112.8 ppm (retention time 24'0).

It also has a 4-hydroxybenzoic acid content of 16.8 ppm (retention time 16'8) and a scirpusin A content of 3.7 ppm (retention time 28'6) and a scirpusin B content of 9.0 ppm (retention time 26'7).

Example 2: Coconut Shell Extract Obtained by Extraction with Subcritical Water

The extraction process of Example 2 is carried out as follows: 16.5 grams of crushed coconut shells (particle size of 1 to 2 mm) are placed into a 30 ml reactor in a study previously heated to 150° C., then the water is pumped through the reactor, under the following operating conditions:

Flow rate: 2 mL/minute
Water temperature: 200° C.
Pressure: 30 bars
Final volume of extract: 100 mL The polyphenol extract obtained is directly analyzed in HPLC. To do this, the solution is filtered through a 0.45 μm PTFE filter and 10 μl of solution are then injected onto a Prontosil column (C18, reverse phase, 250×4.6 mm, 5 μm). The solvents used are: A: H2O/TFA 1% (1 L/5 mL) and B: ACN/TFA 1% (1 L/5 mL). The separation gradient is as follows, at a flow rate of 0.8 mL/minute:

TABLE 1

Gradient separation used in HPLC-DAD

| Time (min.) | % B |
|---|---|
| 0 | 0 |
| 35 | 55 |
| 36 | 100 |
| 37 | 100 |
| 38 | 0 |
| 40 | 0 |

Figure 2:
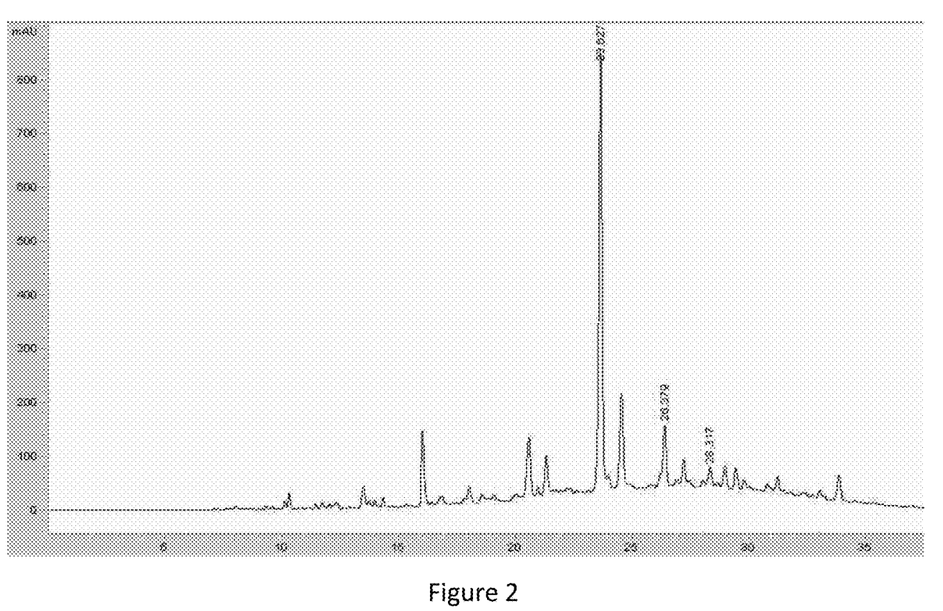
FIG. 2 shows the chromatogram at 306 nm of the extract of Example 2 according to the invention.

The HPLC profile (chromatogram at 306 nm) of the extract obtained is shown in FIG. 2. The extract obtained using this process has a total polyphenol content of 2.43 mg/mL of liquid extract and a trans-piceatanol content of 129 ppm (retention time 23'6). The extract also contains 601.5 ppm of 4-hydroxybenzoic acid (retention time 17 min), 10.5 ppm of scirpusin A (retention time 28'3), and 21.3 ppm of scirpusin B (retention time 26'3).

Example 3: Compositions Containing a Coconut Extract According to the Invention

The examples of compositions given below illustrate the invention without limiting its scope. The percentages are indicated by weight relative to the total weight of the composition.

A protective cream with coconut shell extract base according to Example 1 having the composition indicated below is prepared according to the usual methods:

Anti-wrinkle protective cream

| Phase | Ingredient | % |
|---|---|---|
| A | Water | 80.8 |
| A | Glycerin | 4.5 |
| B | Carboxyvinylic Polymer | 0.8 |
| C | Shea Butter | 1.5 |
| C | Tocopherol | 0.7 |
| C | Caprylic/Capric triglyceride | 7.0 |
| D | Sodium PCA | 1.0 |
| E | Bisabolol | 0.2 |
| F | Coconut Shell Extract | 3.0 |
| G | Fragrance | 0.5 |

The aqueous phase A is heated to 80° C., then phase B is added to form a gel. The fatty phase C is heated to 80° C. and then mixed with the gel while stirring. Phases D to F are added successively at 50° C., then the whole mixture is cooled progressively. Finally, the fragrance is added at 40° C. This emulsion can be applied twice a day on the areas to be treated, particularly "crow's feet" wrinkles and the forehead.

A serum with a coconut shell extract base according to Example 2 having the composition indicated below is prepared according to the usual methods:

Lightening serum

| Phase | Ingredient | % |
|---|---|---|
| A | Water | 86.2 |
| A | Vegetal Glycerin | 3.0 |
| A | Xanthan Gum | 0.5 |
| B | Sodium Hyaluronate | 0.2 |
| B | Vegetal Squalan | 5.0 |
| B | Fragrance | 0.5 |
| B | Cetearylic Alcohol | 2.0 |
| C | Coconut Shell Extract (AND) Vegetal Glycerin | 2.0 |
| C | Phenoxyethanol | 0.6 |

The components of phase A are warm-mixed in the usual way to form a gel, then the phases B and C are successively added to form a serum which can be used for skin care, particularly for lightening the skin or treating brown spots. This serum can be applied once or twice a day to the areas to be treated.

An Eau de Soin with a coconut shell extract base according to Example 2 having the composition indicated below is prepared according to the usual methods:

Eau de soin anti-ageing

| Phase | Ingredient | % |
|---|---|---|
| A | Water | 49.0 |
| A | Rose centifolia Hydrolat | 40.0 |
| A | Coconut Shell Extract | 10 |
| A | Benzylic Alcohol (AND) Dehydroacetic acid (AND) water | 0.6 |
| A | Sodium Hyaluronate | 0.4 |

This eau de coin can be applied once or twice a day to the areas to be treated, notably the face.

Evaluation of the Characteristics and Effectiveness of the Extracts and Compositions According to the Invention Trial 1: Particularity of the Coconut Shell: Characterization of the Different Parts of the Nut (Fluff, Shell, Pulp)

Figure 3A:
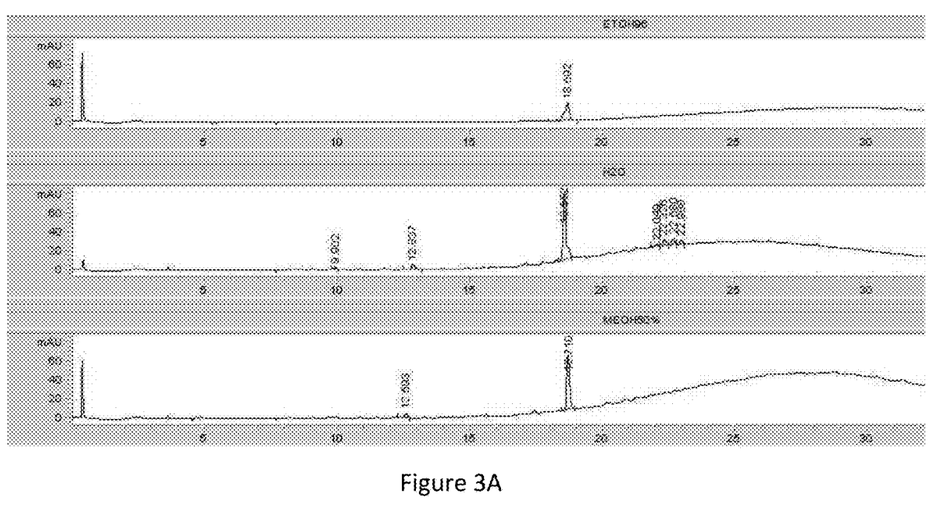
FIG. 3A shows the chromatograms at 280 nm of three extracts (96% ethanol, water and methanol/water 50/50 (v/v) from top to bottom) of fibrous coconut mesocarp.
Figure 3B:
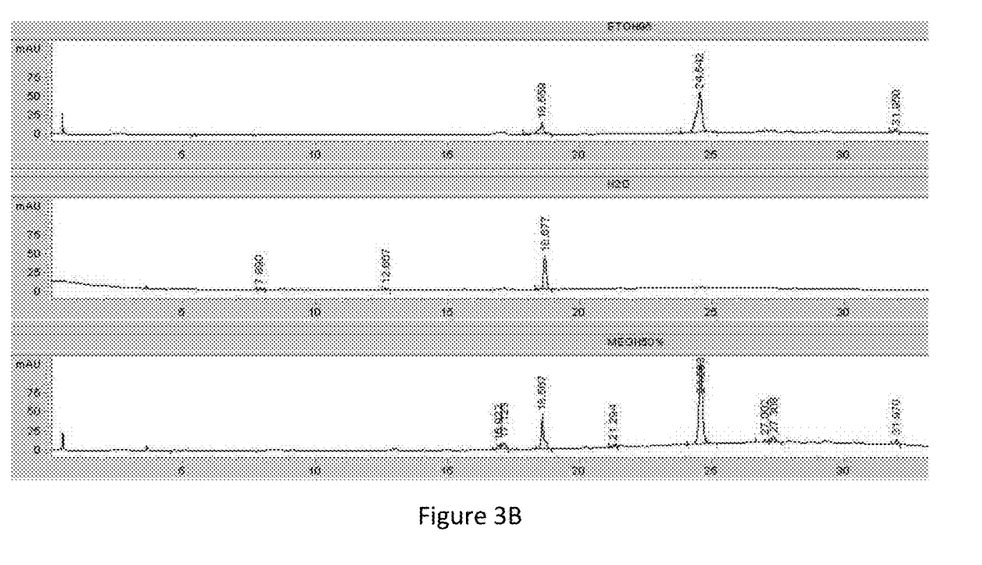
FIG. 3B shows the chromatograms at 280 nm of three extracts (ethanol 96%, water and methanol/water 50/50 (v/v) from top to bottom) of coconut shell.
Figure 3C:
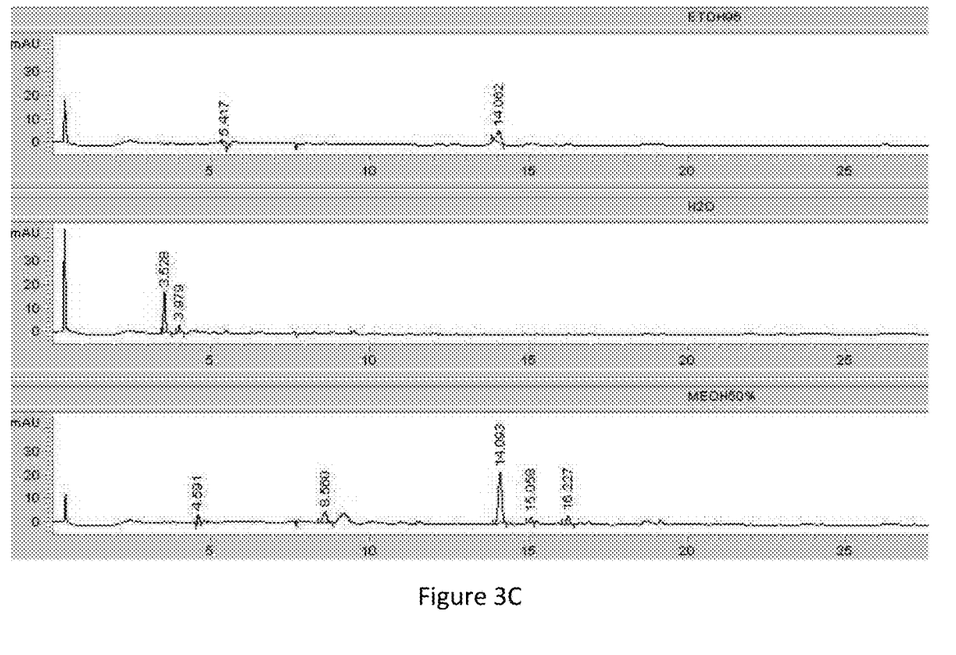
FIG. 3C shows the chromatograms at 280 nm of three extracts (ethanol 96%, water and methanol/water 50/50 (v/v) from top to bottom) of coconut pulp.

The different parts of a coconut (origin: Reunion Island) are separated separately: fibrous mesocarp (fluff), endocarp (shell) and albumen (pulp). About 1 gram of each is extracted with 5 ml of solvent (ultrapure water or methanol/water 50/50 (v/v) or ethanol 96%) for 30 minutes by ultrasound then continuous stirring overnight at room temperature. After centrifugation (9000 rpm, 10 minutes), the supernatant is filtered (0.45 µm, Millipore) and then 15 µL are injected in HPLC with DAD detection. The chromatograms at 280 nm of the different extracts from the different parts of the fruit are shown in FIGS. 3A (fluff), 3B (shell) and 3C (pulp).

As shown in FIG. 3B, in the case of the shell extract, a peak was detected at around 24'5 minutes. This compound could be identified by comparison to a commercial standard (AG-CN2-0086-M025, Coger) as being a trans-piceatanol. As shown in FIGS. 3A and 3C, trans-piceatanol is absent in the other parts of the fruit (fluff, pulp). On another note, other compounds of the same family as piceatannol (stilbenes) were identified in the shell extract only: two piceatanol dimers, scirpusin A (retention time 29'3) and scirpusin B (retention time 27'3). These compounds could be identified in comparison to commercial standards (LGC standards, ref 57349-84 and ref 57348-94). Finally, FIG. 3B shows that a large amount of compound was detected at a retention time of 17'5. This compound could be identified, in comparison to a commercial standard (Sigma-Aldrich, ref 240141), as being 4-hydroxybenzoic acid.

Trial 2: Evaluation of the Antioxidant Effect of Coconut Shell Extracts

The antioxidant properties of the shell extracts of Example 1 and Example 2 were evaluated using ORAC and DPPH chemical tests.

The ORAC test is based upon the prevention of the oxidation of a fluorescent probe, fluorescein, by peroxyl radicals generated by an oxidant, AAPH (2.2'-azobis (2-methylpropionamidine) dihydrochloride). This test is applied according to the method of Ou (Ou et al., 2001), modified by Davalos (Davalos et al., 2004). The reaction is carried out in a 96-well plate in a phosphate buffer. Fluorescein is added to the test extract solution and the plate is pre-incubated for 25 minutes at 37° C. The AAPH solution is added and the fluorescence is recorded for 90 minutes at the excitation and emission wavelengths of 485 and 530 nm respectively. A standard range of Trolox® is produced under the same conditions. Area Under Curve (AUC) is calculated for each sample by integrating the relative fluorescence curve. A regression line is established between the area under curve and the Trolox® concentration; the antioxidant potential of the tested extracts is expressed in equivalent concentration of Trolox® (µmol/100 g of liquid extract).

Regarding the DPPH test: the radical DPPH·+ (2.2-diphenyl-1-picryl-hydrazyl) is stable at an ordinary temperature and has a characteristically blue color. The antioxidants present in the testing extracts reduce it, which results in a discoloration easily measurable by spectrophotometry at 517 nm. The method is generally standardized with respect to Trolox®. To evaluate the antioxidant activity, the reactivity is estimated by the effective concentration ($EC_{50}$) of the antioxidant, which corresponds to a 50% reduction of activity (of absorbance) of the DPPH in the reaction medium. $EC_{50}$ is expressed as the concentration of the liquid extract (%).

The obtained results are presented in the following Table 1:

TABLE 1

Antioxidant activity of coconut shell extracts

| Extract | ORAC (µmole Trolox ®/100 g) | DPPH ($EC_{50}$, %) |
|---|---|---|
| Example 1 | 1215 ± 92 | 1.04 ± 0.06 |
| Example 2 | 9330 ± 432 | 0.23 ± 0.01 |

These results show that coconut shell extracts have significant antioxidant activity. In addition, it is found that the subcritical water extract has a significantly higher antioxidant activity than the extract obtained by maceration in the solvent methanol/water 50/50 (v/v).

Thus, by acting on the trapping of free radicals, the extracts according to the invention can delay the effects of aging on the skin.

Trial 3: Evaluation of the Effect on the Inhibition of Glycation

An in tubo model was used to evaluate the effects of coconut shell extract. It is based on the measurement of the formation of derivatives of the glycation reaction between the free amino groups of bovine albumin and glucose. Some of these derivatives, advanced glycation end products (AGES), are fluorescent. A reference molecule, aminoguanidine, is tested in parallel. The system test is a reaction mixture containing bovine albumin (1 mg/ml) and glucose (1.25 M) in a phosphate buffer D-PBS pH 7.4.

The products are mixed for the test system in sterile tubes and then placed in a water bath at 60° C. for 24 hours. After cooling, 70 µl of 100% (p/v) trichloroacetic acid are added to the reaction mixture and the tubes are then placed at −20° C. for 30 minutes. After centrifugation (10 minutes, 9000 rpm), the bottom layer is retaken in a D-PBS buffer (pH 10). 150 µl of each tube are removed and transferred to a 96-well black plate. The fluorescence is then read using a spectrofluorometer (FLUOstar, BMG Labtech) at excitation wavelengths at 370 nm and emission wavelengths at 440 nm.

Figure 4:
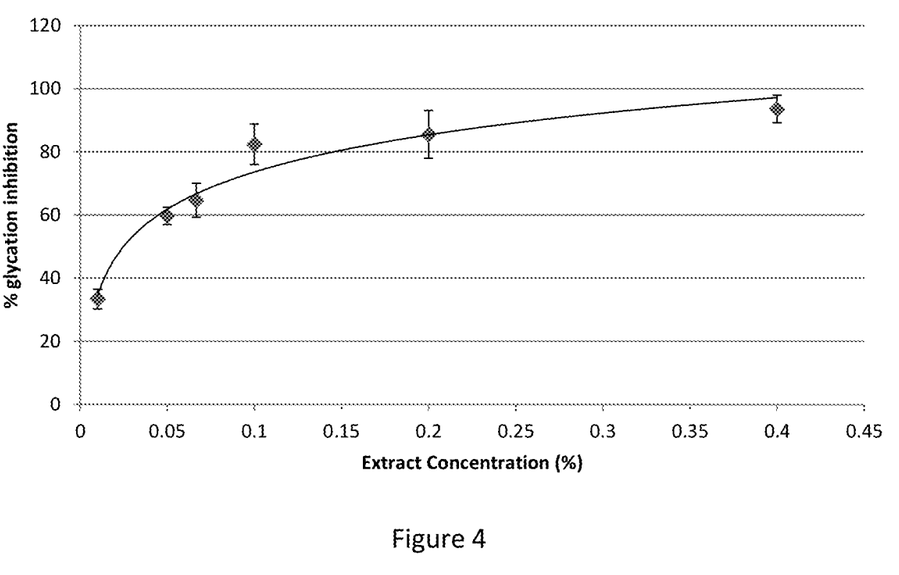
FIG. 4 represents the dose-response curve of the inhibition of glycation by the extract of example 2.

The extract of Example 2 was tested at different concentrations: 0.4%, 0.2%, 0.1%, 0.06%, 0.05% and 0.01%. The results are shown in FIG. 4.

It is noted that the coconut shell extract of Example 2, starting at the 0.05% dose, causes a 59.7% inhibition of the glycation of the albumin induced by glucose. At a higher dose (0.4%), the coconut shell extract of Example 2 causes a 93.5% inhibition of glycation.

The extracts according to the invention can therefore be used for anti-aging care, particularly to prevent aging of the skin induced by glycation.

Trial 4: Evaluation of the Effect on the Inhibition of Tyrosinase

In the melanin biosynthetic chain, tyrosinase catalyzes the formation of dopaquinone and then dopachrome from L-DOPA. Dopachrome is a colored compound whose appearance can be monitored by spectrophotometry.

The use of tyrosinase inhibitors leads to a limited production of melanin. This method is commonly used in dermocosmetics to whiten and unify the complexion of the skin or to reduce brown spots due to skin aging. The molecules described as tyrosinase inhibitors can act by several mechanisms. They can interfere with the transcription of its gene, its glycosylation, reduce the post-transcriptional control, or inhibit its activity by different means. Most depigmenting agents work by inhibiting the activity of tyrosinase. These products can be substrate analogs, competitive inhibitors or even copper chelators, a co-factor essential for tyrosinase activity.

In the present study, the anti-tyrosinase activity of the extracts described in the invention were found on the mushroom tyrosinase. The advantage of the latter is its commercial availability in a purified form, which offers the possibility of conducting reliable enzyme studies. It is therefore used here as a screening model.

The coconut shell extracts to be tested are diluted in sodium phosphate buffer pH 7.2 then incubated with the tyrosinase (Tyrosinase from Mushroom>1000 U/mg (ref Sigma T3824)) at 9 U/wells for 5 minutes at 37° C. in a 96-well plate. The tyrosine (ref Sigma T2900000, 2 mM) is then added to the mixture and the reaction is studied by reading the DO at 492 nm for 5 minutes (appearance of dopachrome) with the help of a spectrophotometer with microplate reader. A negative control is completed with adding the extract (buffer).

Calculating the inhibition of the tyrosinase activity by the extracts is done by comparing the DO of the extract to the DO of the negative control (without extract). The dilution of the extracts which inhibit 50% of tyrosinase activity ($IC_{50}$) is calculated following the dosage-response curve.

The extract in example 1 was tested at different concentration levels: 0.3%, 0.6%, 1.2%, 2.4 and 4.8%. The results are presented in FIG. 5A.

Figure 5A:
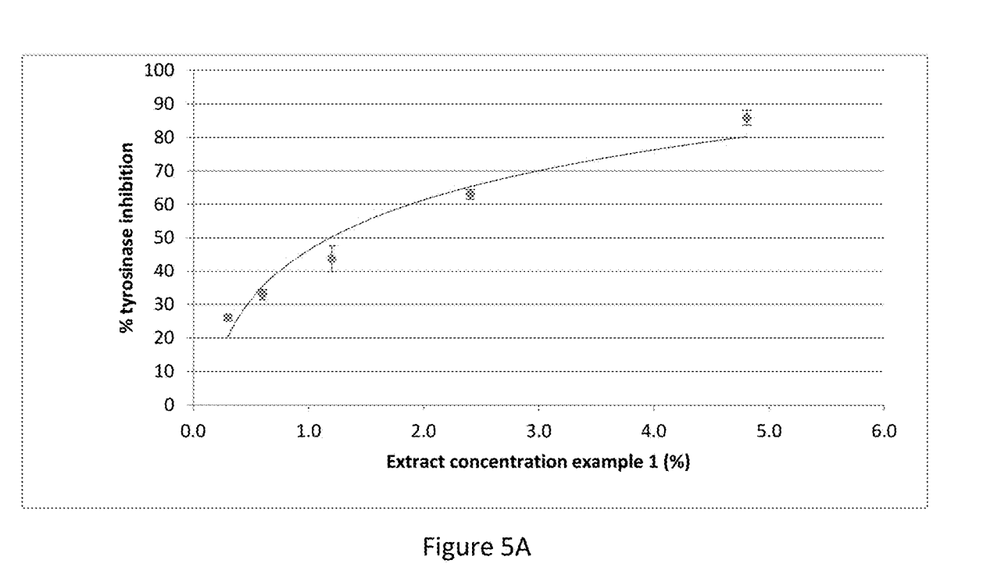
FIG. 5A represents the dose-response curve of the inhibition of tyrosinase activity by the extract of example 1.

It can be observed that the coconut shell extract in example 1, starting at a dose of 0.6% provoked an inhibition of 32.9% of tyrosinase activity. At a stronger dosage (1.2%), the coconut shell extract from example 1 brought on 50% inhibition of tyrosinase.

The extract of example 2 was tested at different concentration levels: 0.3%, 0.6%, 1.2%, 2.4 and 4.8%. The results are presented in FIG. 5B.

Figure 5B:
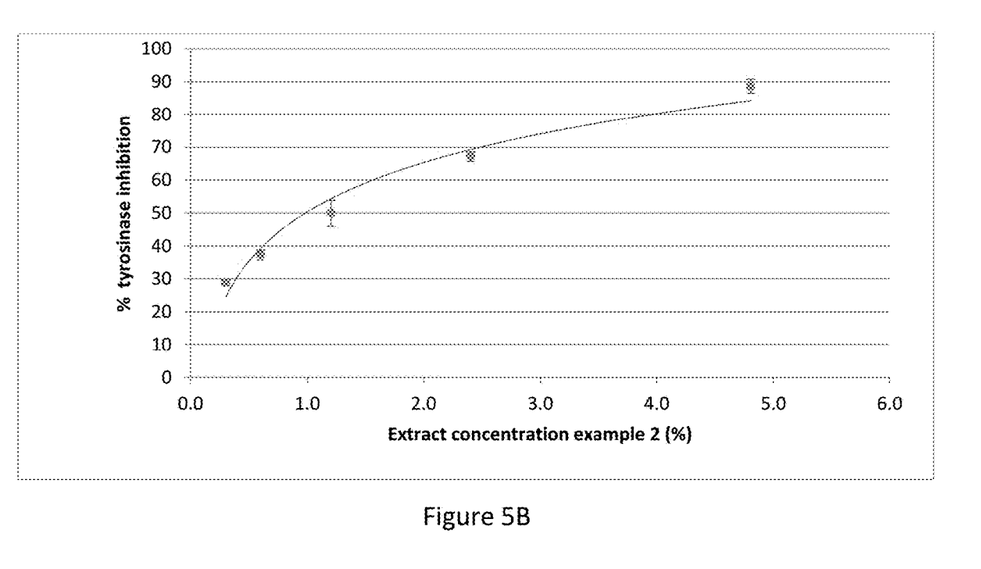
FIG. 5B represents the dose-response curve of the inhibition of tyrosinase activity by the extract of Example 2.

It can be observed that the coconut shell extract in example 2, starting at a dose of 0.6% provoked an inhibition of 37.2% of tyrosinase activity. At a stronger dosage (1%), the coconut shell extract in example 2 brought on a 50% inhibition of tyrosinase.

The coconut shell extracts according to the invention can thus be used for skin depigmentation application.

Trial 5: Evaluation of the Effect on Gene Expression in Human Keratinocytes

The effects of the coconut shell extract tested according to the invention (extract of Example 2) were researched on gene expression in normal human epidermal keratinocytes (NHEK). More precisely, a transcriptomic analysis was performed using the Affymetrix GeneAtlas platform and the "full transcriptome human" U219 chip containing 36000 transcripts and variants.

The keratinocytes were inoculated in a 24-well plate (NHEK) and grown in a culture environment for 48 hours with renewal of the medium after 24 hours of incubation, then in a test medium for an additional 24 hours. The medium was then replaced with test medium containing or not (Control) the coconut shell extract, and then the cells were incubated for 24 hours. All the experimental conditions were completed in n=3. At the end of the incubation, the culture supernatants were removed and the cell mats were rinsed with PBS solution. The plates were immediately dry frozen at −80° C. Before extraction, culture replicates were pooled. The total RNA of each sample was extracted using TriPure Isolation Reagent® according to the protocol recommended by the supplier. The quantity and quality of the RNA were evaluated by capillary electrophoresis (Bioanalyzer 2100, Agilent). The synthesis of biotinylated antisense RNA (RNAa) was carried out using the "GeneChip 3'IVT Express" kit (Affymetrix®). For each biotinylated RNAa sample an electrophoretic profile was made (Bioanalyzer 2100, Agilent) before and after fragmentation. Hybridization of the labeled and fragmented RNAa on the Affymetrix® U219 chip (36,000 transcripts and variants) was performed on the GeneAtlas™ fluidics Affymetrix® hybridization station for 20 hours at 45° C. The U219 chips were then scanned using the GeneAtlas™ Imaging station (Affymetrix®-2 µm resolution) to generate the signal strength data. Signal strength data was standardized using the Expression Console software)(Affymetrix®), based on the RMA algorithm. Quality control of the labeling as well as the hybridization was then carried out. The thresholds of "fold change" (value corresponding to the ratio:signal intensity value of a probe corresponding to the treated sample/signal intensity value of a probe corresponding to the Control) have been defined and applied to standardized data. For overexpression of the probe, the Fold Change threshold was set at ≥2 and for a subexpression probe, the Fold Change threshold was set at ≤0.5.

Effects on Epidermal Keratinocytes:

Normal human keratinocytes (NHEK) were treated for 24 hours with the coconut shell extract of Example 2 at a dose of 0.123% (p/v). At the end of the incubation, the gene expression was analyzed by comparison with the Control sample (untreated).

As shown in Table 2, the coconut shell extract of Example 2 greatly increased the expression of certain markers of cell detoxification and DNA repair:

TABLE 2

Relative expression of genes in the keratinocytes treated or not by the coconut shell extract of example 2

| Gene | Control (non treated) | Coconut shell extract (0.123%) | Fold change |
|---|---|---|---|
| CYP1B1 | 26.72 | 307.04 | 11.49 |
| CYP1A1 | 52.40 | 484.33 | 9.24 |
| RAD23B | 115.53 | 372.82 | 3.23 |

CYP1B1 and CYP1A1 (cytochrome P450): the CYP1B1 and CYP1A1 genes encode enzymes in the cytochrome P450 superfamily. Cytochromes P450 are hemoproteins that are involved in the oxidation-reduction reactions of numerous molecules, whether metabolites or xenobiotics (pollutants, toxins, drugs, medication, etc.).

RAD23B: This is a gene coding for a nucleotide excision repair (NER) protein, one of our natural systems for repairing degraded DNA (for example by ultraviolet exposure). It slows the aging of the body, limits deleterious mutations and the risk of tumors and cancer.

These results are in favor of a reinforcement of cellular defense mechanisms, notably the detoxification and repair of epidermal cell DNA by the coconut shell extract.

The invention claimed is:

1. A liquid or solid coconut shell extract comprising trans-piceatannol in a quantity representing:
   between 50 and 200 ppm by weight of liquid extract if it is liquid, the liquid extract further comprising between 2 and 20 ppm of scirpusin A and between 5 and 50 ppm of scirpusin B by weight of the liquid extract, or
   between 0.2% and 0.8% by weight of dry extract if it is in solid form, the extract in solid form further comprising between 0.008 and 0.08% scirpusin A and between 0.02 and 0.2% scirpusin B by weight of dry extract in solid form, and wherein the extract is obtained by solid-liquid extraction with water in the subcritical state as an extraction solvent.

2. The coconut shell extract according to claim 1, further comprising between 10 and 1000 ppm of hydroxybenzoic acid by weight of liquid extract when the extract is liquid or between 0.04 and 4% of hydroxybenzoic acid by weight of dry extract when the extract is in solid form.

3. The coconut shell extract of claim 1, wherein the coconut shell is dried and ground before being extracted.

4. A method for obtaining an extract according to claim 1, comprising a subcritical water extraction carried out at a temperature between 100° C. and 220° C. and at a pressure above 20 bar, sufficient to maintain the water in the liquid state.

5. The coconut shell extract according to claim 1, wherein the subcritical water extraction is carried out at a temperature between 100° C. and 220° C. and at a pressure above 20 bar, sufficient to maintain the water in the liquid state.

6. The coconut shell extract according to claim 1, wherein the subcritical water extraction is carried out at a temperature between 120° C. and 200° C. and a pressure between 20 and 50 bars.

7. A cosmetic and/or dermatological composition for topical application, comprising as active principle the coconut shell extract of claim 1.

8. The cosmetic and/or dermatological composition according to claim 7, comprising from 0.01 to 10% by weight of coconut shell extract relative to the total weight of the composition.

9. The cosmetic and/or dermatological composition according to claim 7, wherein the composition is in the form of cream, emulsion, milk, ointment, lotion, oil, aqueous solution, hydro-alcoholic solution, glycolic solution, powder, patch or spray.

10. The cosmetic and/or dermatological composition according to claim 7, wherein the coconut shell extract is a liquid extract stabilized with glycerin before incorporation into the composition.

11. A cosmetic method comprising applying to the skin a cosmetic composition according to claim 7.

12. The cosmetic method according to claim 11, for reducing and/or treating signs of aging of the skin and/or mucous membranes and/or hair.

13. The cosmetic method according to claim 12, for lightening the complexion of the skin and/or reducing brown spots on the skin.

14. The cosmetic and/or dermatological composition according to claim 7, further comprising stabilizing the coconut shell extract with glycerin before incorporation into the composition.

* * * * *